(12) United States Patent
Docherty

(10) Patent No.: US 6,197,834 B1
(45) Date of Patent: Mar. 6, 2001

(54) METHOD OF INHIBITING FORMATION OF INFECTIOUS HERPES VIRUS PARTICLES

(75) Inventor: John Docherty, Kent, OH (US)

(73) Assignee: Northeastern Ohio Universities College of Medicine, Rootstown, OH (US)

( * ) Notice: Subject to any disclaimer, the term of this patent is extended or adjusted under 35 U.S.C. 154(b) by 0 days.

(21) Appl. No.: 09/145,039

(22) Filed: Sep. 1, 1998

(51) Int. Cl.$^7$ .................................................. A61K 31/05
(52) U.S. Cl. ................................................ 514/733
(58) Field of Search ............................................ 514/733

(56) References Cited

U.S. PATENT DOCUMENTS 5,500,367 * 3/1996 Aain et al. ........................ 435/252.3

OTHER PUBLICATIONS

"Oxidative Stress During Viral Infection: A Review" by Kathleen B. Schwarz, *Free Radical Biology & Medicine*, vol. 21, No 5, 1996, pp. 641–649.

"Effect of Stilbene Derivatives on Gastric H+, K+–ATPase" by Murakami, et al., *Biochemical Pharmacology*, vol. 44, No. 10, 1992, pp. 1947–1951.

"Antioxidants Selectively Suppress Activation of NF–κB by Human T–Cell Leukemia Virus Type 1 Tax Protein" by Schreck, et al., *Journal of Virology*, vol. 66, No, 11, Nov., 1992, pp. 6288–6293.

"Resveratrol Arrests the Cell Division Cycle at S/G2 Phase Transition" by Ragione, et al., *Biochemical and Biophysical Research Communications*, 250, 1998 pp. 53–58.

"Cancer Chemopreventive Activity of Reveratrol, a Natural Product Derived from Grapes" by Jang, et al., *Science*, vol. 275, Jan. 10, 1997, pp. 218–220.

"Resveratrol Arrests the Cell Division Cycle at S/G2 Phase Transition" by Ragione, et al., *Biochemical and Biophysical Research Communications*, 250, 1998 pp. 53–58.

"Evaluation of antioxidant healing formulations in topical therapy of experimental cutaneous and genital herpes simplex virus infections" by Sheridan, et al., *Antiviral Research*, 36, 1997, pp. 157–166.

"Resveratrol, a remarkable inhibitor of ribonucleotide reductase" by Fontecave, et al., *FEBS Letters*, 421, 1998, pp. 277–279.

Jang et al, *Science* vol. 275 pp. 218–222, 1997.*

Rapp et al, CA92:69943, 1979.*

* cited by examiner

*Primary Examiner*—Russell Travers
(74) *Attorney, Agent, or Firm*—Calfee, Halter & Griswold LLP

(57) ABSTRACT

The present invention provides a method of inhibiting the formation of infectious herpes virus particles, particularly infectious herpes simplex virus (HSV) particles, in a host cell. The method involves administering an effective amount of a hydroxylated stilbene, particularly resveratrol, to a herpes virus infected host cell. The present invention also provides a method of treating a herpes virus infection, particularly an HSV infection. The method comprises administering a topical composition comprising a therapeutically effective amount of a hydroxylated stilbene to a herpes virus-infected site. The present invention also relates to a topical composition for treating a herpes virus infection selected from the group consisting of an HSV infection, a cytomegalovirus infection, and a varicella zoster virus infection. The present invention also provides a method of reducing the cytopathic effect of HSV on mammalian cells. The method involves administering resveratrol to the host cell, either in vitro or in vivo, in an amount sufficient to inhibit replication of HSV-1 or HSV-2 within the host cell.

16 Claims, 4 Drawing Sheets

METHOD OF INHIBITING FORMATION OF INFECTIOUS HERPES VIRUS PARTICLES

BACKGROUND

Human herpes viruses can infect host cells in virtually any organ of the human body. Replication of a herpes virus within an infected host cell leads to lysis of the infected cell and the release of large numbers of infectious virus. The infectious particles released from the lysed cell can infect and destroy other cells at or near the site of the initial infection. These infectious particles can also be transmitted to a non-infected individual. These infectious particles can also enter and remain latent, i.e., in the non-replicative state, in other cells of the afflicted individual for life. This life-long infection serves as a reservoir of infectious virus for recurrent infections in the afflicted individual and as a source of infection for an unwitting contact.

At least four of the human herpes viruses, including herpes simplex virus type 1 (HSV- 1), herpes simplex virus type 2 (HSV-2), cytomegalovirus (CMV), and varicella zoster virus (VZV) are known to infect and cause lesions in the eye of certain infected individuals. Together, these four viruses are the leading cause of infectious blindness in the developed world.

HSV-1 primarily infects the oral cavity, while HSV-2 primarily infects genital sites. However, any area of the body, including the eye, skin and brain, can be infected with either type of HSV. Generally, HSV is transmitted to a non-infected individual by direct contact with the infected site of the infected individual.

The initial symptoms of a primary or recurrent HSV infection include tingling, pain, and/or parasthesia at the site of infection. This is followed by formation of a lesion at the infected site, i.e., in the oral cavity, eye, skin, or reproductive tract. Healing typically occurs in approximately ten to fourteen days.

The immune reaction that occurs in response to an HSV infection prevents dissemination of the virus thtoughout the body of the immmunocompetent individual. Such immune reaction. however, does not eliminate all infectious HSV particles from the body of the afflicted individual. The virus particles that are not killed by the immune response move along the nerve path to the ganglia of the infected individual where they remain in a state of latency. In response to a variety of stimuli including stress, environmental factors, other medications, food additives or food substances, the infectious virus particles may leave the ganglia and cause a recurrent infection at or near the original site of infection. In those HSV-infected individuals who are immunosuppressed or who lack a well-developed immune system, such as neonates, dissemination of the virus particles from the infected site can also occur and lead to life-threatening complications, including encephalitis.

VZV, which is transmitted by the respiratory route is the cause of chickenpox, a disease which is characterized by a maculopapular rash on the skin of the infected individual. As the clinical infection resolves, the virus enters a state of latency in the ganglia, only to reoccur in some individuals as herpes zoster or "shingles" The reoccurring skin lesions remain closely associated with the dermatome, causing intense pain and itching in the afflicted individual.

CMV is more ubiquitous and may be transmitted in bodily fluids. The exact site of latency of CMV has not been precisely identified, but is thought to be leukocytes of the infected host. Although CMV does not cause vesicular lesions, it does cause a rash.

There are no known cures for infections with human herpes viruses, i.e., methods of eliminating the virus from the body of the infected individual. In addition, there are very few methods for blocking the formation of infectious herpes virus particles and thereby reducing the frequency, severity, or duration of a herpes virus-induced infection and the likelihood of recurrence of infection in the latently-infected individual.

Thus, it is desirable to have additional methods for inhibiting the formation of infectious herpes virus particles. Such method is useful for limiting the severity of a herpes virus infection within an infected individual and the likelihood of transmission of the herpes virus infection from the infected individual to a non-infected individual.

SUMMARY OF THE INVENTION

The present invention provides a new method of inhibiting the formation of infectious herpes virus particles, particularly infectious HSV particles, in a host cell. The method involves administering a hydroxylated stilbene, particularly resveratrol, to a herpes virus infected host cell. The hydroxylated stilbene is administered to the host cell in an amount sufficient to inhibit replication of the virus in the virus-infected host cell. Such method is useful for reducing the cytopathic effect of a herpes virus infection. Such method is also useful for preventing the spread of the herpes virus from a virus-infected host cell to a non-infected host cell. Such method is also useful for establishing a model system for studying the molecular events that occur during replication of herpes virus and for studying the factors that trigger replication of a latent herpes virus, particularly replication of latent HSV.

The present invention also provides a method of treating a herpes virus infection, particularly an HSV infection. The method comprises administering a topical composition comprising a therapeutically effective amount of a hydroxylated stilbene, particularly resveratrol, to a herpes virus-infected site. The present invention also relates to a topical composition for treating a herpes virus infection selected from the group consisting of an HSV infection, a CMV infection, and a VZV infection.

The present invention also provides a method of reducing the cytopathic effect of HSV on mammalian cells. The method involves administering resveratrol to the host cell, either in vitro or in vivo, in an amount sufficient to inhibit replication of HSV-1 or HSV-2 within a virus-infected host cell.

DETAILED DESCRIPTION OF THE INVENTION

Figure 1:
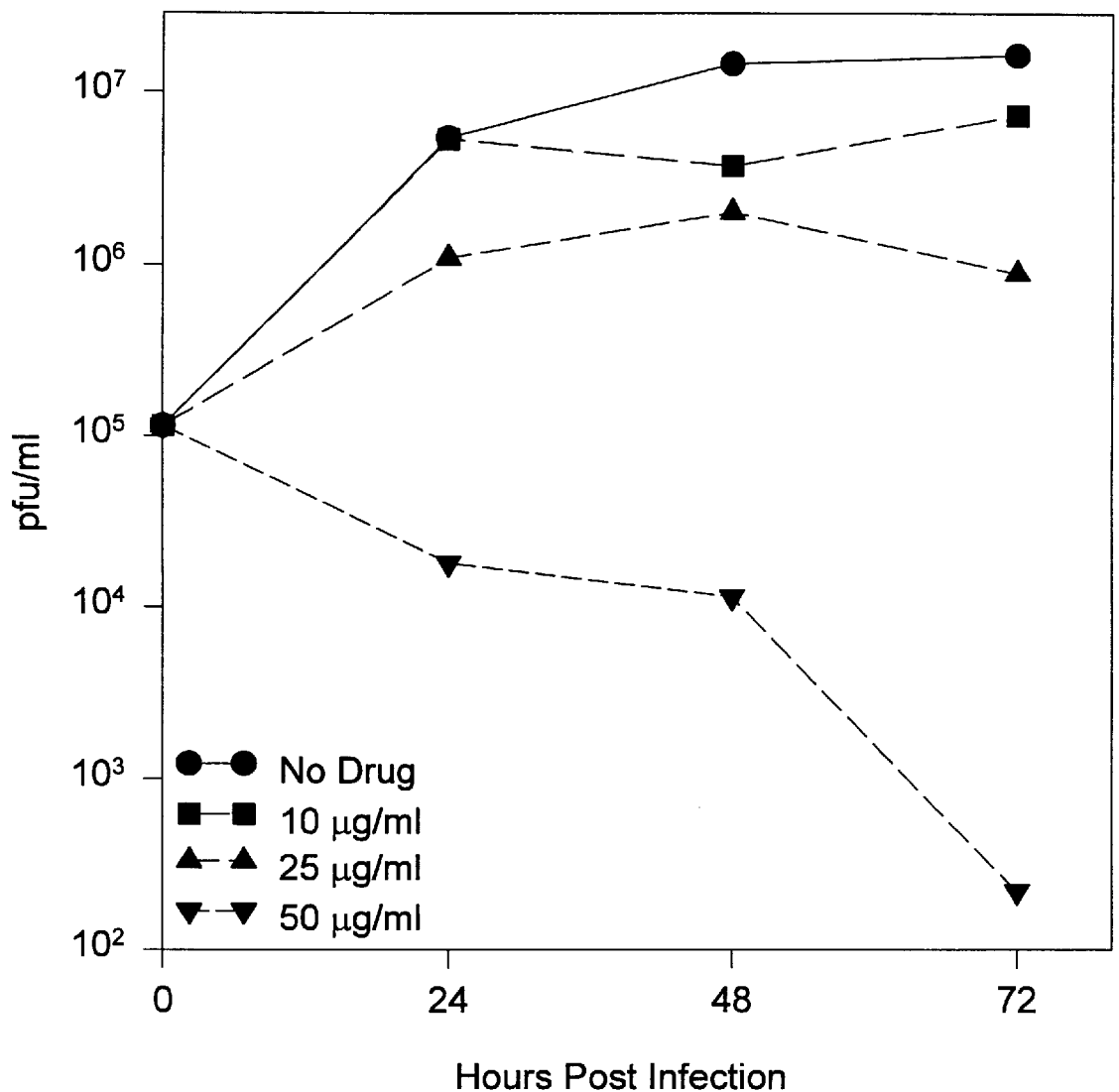
FIG. 1 is a graph showing the extent of HSV-1 replication in virus-infected cells treated with different concentrations of resveratrol.

In one aspect, the present invention provides a method of inhibiting formation of infectious herpes virus particles, particularly infectious HSV particles, in a host cell. The method comprises administering a hydroxylated stilbene to the host cell. The hydoxylated stilbene is administered in an amount sufficient to or effective to inhibit replication of the herpes virus within the infected cell. Preferably, the hydroxylated stilbene, is administered to the host cell either prior to infection of the host cell with the virus or preferably, within six hours after infection of the host cell with the virus.

Preferably, the hydroxylated stilbene is administered to the host cell by contacting the host cell with or exposing the host cell to a composition comprising the hydroxylated stilbene. For example, in vitro, the method comprises adding a hydroxylated stilbene to the culture medium of herpes virus-infected host cells. In the case of cultured cells, the hydroxylated stilbene is added to the medium, preferably before the host cells are infected with the virus or within six hours after the host cells are infected with the virus. In the case of ganglia, which serves as an organ culture model system for studying latency of herpes viruses, particularly for studying latency of HSV, the hydroxylated stilbene is added to the medium after the ganglia are excised from the latently-infected host. With respect to HSV, good results have been obtained by exposing cultured host cells or HSV-infected ganglia to the hydroxylated stilbene, resveratrol, at a concentration which is greater than 10 $\mu$g/ml and less than 100 $\mu$g/ml of culture medium.

It has been determined that treatment of cultured cells in accordance with the present method is non-toxic to cells and blocks replication of HSV at some early stage in the replicative cycle of this human herpes virus. It has also been determined that the effect of resveratrol on HSV replication is reversible. Typical of the herpes viruses, HSV replication occurs in phases, with each phase being dependent on the successful completion of the prior phase. The "immediate early phase" occurs at 1–3 hours after infection and is associated with regulatory and synthetic events. The "early phase" occurs 3–6 hours after infection and is also associated with regulatory and synthetic events, particularly the synthesis of virus DNA. The "late phase" occurs 6–10 hours after infection and is associated with final synthetic events and assembly of viral components into infections virions. Accordingly, since all herpes viruses have in common a replicative scheme that progresses through similar and distinct phases, such method is useful for establishing model systems for studying the molecular events that occur during replication of all herpes viruses. For example, mammalian cell cultures incubated in the presence and absence of resveratrol may be used to identify cellular factors that are involved in regulating herpes virus synthetic events. Such cell cultures may also be employed to characterize the role of HSV gene products in the replication of infectious virus, particularly those proteins and factors whose function are currently unknown.

Such method is also useftil for establishing a model system for studying latency of herpes viruses, particularly latency of the herpes viruses that remain latent in the ganglia, such as for example HSV and VZV. Such model system is useful for characterizing the extracellular factors such as for example hormones and cytokines, as well as the intracellular factors and molecular events that trigger replication of latent herpes viruses.

In another aspect, the method comprises administering a pharmaceutical composition, preferably a topical composition, comprising a therapeutically effective amount of a hydroxylated stilbene, preferably resveratrol, to the site of the infection. As used herein "site of the infection" means a previously uninfected site which is expected to come into contact with a herpes virus-infected site or the site of a current or prior herpes virus-induced lesion. Such method is particularly useful for treating local herpes virus infections, such as for example, HSV-induced skin lesions, HSV-induced eye infections, HSV-induced lesions of the reproductive tract, CMV-induced eye lesions, and VZV-induced eye lesions. In such cases, it is preferred that the hydroxylated stilbene, more preferably resveratrol, be applied directly to the infected site. It is preferred that the hydroxylated stilbene be administered to the herpesvirus-infected site in the form of an aqueous solution or in the form of a salve. For eye infections, it is preferred that an aqueous solution of the hydroxylated stilbene, more preferably resveratrol, be administered as an eye drop. For herpesvirus skin lesions, such as for example, HSV-induced skin lesions, or HSV-induced lesions of the reproductive tract, it is preferred that the composition be applied topically.

HYDROXYLATED STILBENES

The structural skeleton, of the compound employed in the present invention, i.e., the hydroxylated stilbene, comprises two aromatic rings joined by a methylene bridge. Preferably, the hydroxylated stilbene is a polyhydroxylated stilbene, more preferably a trihydroxystilbene or a tetrahydroxystilbene, most preferably the tri-hydroxylated stilbene, 3,5,4'-trihdyroxystilbene, also known as resveratrol, or a derivative thereof. Resveratrol in either the cis form or trans form is suitable. Derivatives of resveratrol as used herein refers to compounds in which one or two of the hydroxyl functions of resveratrol are replaced with other moieties such as, for example, pterostilbene in which the hydroxyl functions at positions 3 and 5 on the disubstituted aromatic ring are methoxylated and the $\beta$-glucoside derivative polydatin or piceid, in which one of the hydroxyl functions on the disubstituted aromatic ring is replaced with glucose; as well as polymers of the parent compound resveratrol. Such polymers have been given the name viniferins. Methods for producing the hydroxylated stilbenes are described in Moreana-Manas, M. et al, Anal Quim (1985) 81:157–161; Jeandet, P. et al, Am J. Enol Vitic (1991) 42:41–6; Goldberg DM et al. Anal Chem (1994) 66:3959–63, Murakami, S et al, Biochem Pharmacol. (1992) 44:1947–51; and Thakkar, K et al, J. Med Chem (1993) 36:2650–51, which are incorporated herein by reference. Resveratrol and 3,3',4,5'-tetrahydroxy-trans-stilbene, known as piceatoannol, are also available commercially from Sigma Chemical Co., St. Louis, Mo.

TOPICAL COMPOSITION

A pharmaceutical composition comprising a therapeutically effective amount of a hydroxylated stilbene, preferably a polyhydroxylated stilbene, more preferably rcsveratrol or a derivative thereof, and a pharmaceutically acceptable carrier, preferably a topical carrier is administered to or proximate to the cells known to be infected with, or suspected of being infected with the virus, or expected to come into contact with infectious virus. Preferably, the composition comprises a relatively inert topical carrier. Many such carriers are routinely used and can be identified by reference to pharmaceutical texts. Examples include polyethylene glycols, polypropylene copolymers, and some water soluble gels. Such a composition, referred to hereinafter as the "topical composition", may also contain diluents, fillers, salts, buffers, stabilizers, solubilizers, and other pharmaceutically acceptable materials well known in the art. The term "pharmaceutically acceptable" means a non-toxic material that does not interfere with the effectiveness of the antiviral activity of the hydroxylated stilbene.

In practicing the present method of treatment or use, a pnarmaceutical composition comprising a therapeutically effective amount of the hydroxylated stilbene, preferably resveratrol, is applied to the site of infection in the host subject before or after the host subject is exposed to the virus. Such composition is particularly effective in treating infections of the eye, oral cavity and vagina as well as border areas of the lips and rectumn. In the case of oral administration, dentrifices, mouthwashes, tooth paste or gels, or mouth sprays are used. Vaginal or rectal administration may be by the usual carriers such as douches, foams, creams, ointments, jellies, and suppositories, the longer lasting forms being preferred. Ocular administration is preferably by ophthalmic ointments or solutions. Lip treatment is, preferably, in the form of a gel.

The topical composition may further contain other agents which either enhance the activity of the hydroxylated stilbene or complement its activity or use in treating the viral disease. Such additional factors and/or agents may be included in the pharmaceutical composition to produce a synergistic effect with the hydroxylated stilbene, or to minimize side effects. The topical composition may also contain an agent which enhances uptake of the hydroxylated stilbene.

Preferably the topical composition comprises a solvent for the hydroxylated stilbene, such as, for example, an alcohol. A liquid carrier such as water, petroleum, oils of animal or plant origin such as peanut oil, mineral oil, soybean oil, or sesame oil, corn oil, or synthetic oils may be added. The liquid form of the pharmaceutical composition may further contain a physiological saline solution, dextrose or other saccharide solution, or glycols such as ethylene glycol, propylene glycol or polyethylene glycol. The preparation of such topical composition having suitable pH, isotonicity, and stability, is within the skill in the art.

The topical composition of the invention may be in the form of a liposome in which the hydroxylated stilbene is combined with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art.

DOSAGE

The hydroxylated stilbene, preferably a polyhydroxylate stilbene, more preferably resveratrol or a derivative thereof is administered to the site of infection in the host subject in a therapeutically effective amount. As used herein, the term "therapeutically effective amount" means the total amount of the hydroxylated stilbene that is sufficient to show a meaningful benefit, i.e., treatment, healing, prevention, amelioration, or reduction in the symptoms of a herpesvirus infection, such as an HSV infection, or an increase in rate of healing, amelioration or reduction in the symptoms of such infection.

By "treating" is meant curing or ameliorating a herpesvirus infection or tempering the severity of the infection. By preventing is meant blocking the formation of a primary lesion or recurrence of a lesion at the infected site. The dosages of the hydroxylated stilbene, particularly resveratrol, which can treat or prevent an HSV, VZV, or CMV infection, particularly an HSV infection, can be determined in view of this disclosure by one of ordinary skill in the art by rumiing routine trials with appropriate controls. Comparison of the appropriate treatment groups to the controls will indicate whether a particular dosage is effective in preventing or treating a virus infection at the levels used in a controlled challenge.

It is contemplated that the various pharmaceutical compositions used to practice the method of the present invention should contain about 0.01 $\mu$g to about 10 mg, more preferably about 0.1 $\mu$ to about 1 mg, of the hydroxylated stilbene, most preferably from about 10 $\mu$g to about 100 $\mu$g of resveratrol per/ml of the composition. Although a single application of the topical composition may be sufficient to ameliorate the pathological effects of the virus, it is expected that multiple doses will be preferred.

DELIVERY

Administration of the pharmaceutical composition is via local administration to the infected site. In those individuals who have experienced a primary lesion, it is preferred that the topical composition be applied at the prodromal stage of infection, i.e., during early symptoms of pain, tingling, parasthesia. Preferably, the composition is applied to the site of infection periodically, more preferably every three hours. The duration of therapy using the pharmaceutical composition of the present invention will vary, depending on the severity of the disease being treated and the condition and response of each individual patient. Ultimately the attending physician will decide on the appropriate duration of using the pharmaceutical composition of the present invention.

The following examples of methods of using resveretrol to block formation of infectious HSV particles in vitro treating HSV infections are for purposes of illustration only and are not intended to limit the scope of the claims which are appended hereto.

Example 1

Inhibiting Formation of Infectious HSV-1 Particles by Treatment with Resveratrol A. Cultures of African green monkey kidney cells (Vero) cells, obtained from the American Type Culture Collection, Rockville, Md., were grown to confluence in Medium 199 supplemented with 5% fetal bovine serum, 0.075% $NaHCO_3$, and 50 $\mu$g/ml gentamycin sulfate in 25 $cm^2$ tissue culture flasks. Cells were infected with HSV-1 at a multiplicity of infection (moi) of one and incubated at room temperature for one hour to allow for virus attachment to and penetration of the cell. Under these conditions, approximately half of the cells are infected with virus. Thereafter, the cultures were rinsed three time with media and incubated in medium containing resveratrol at a final concentration of 10 $\mu$g/ml, 25 $\mu$g/ml, or 50 $\mu$g/ml. Stock solutions of the resveratrol, obtained from Sigma Chemical Co, St. Louis, Mo. were prepared in 100% ethanol and diluted to the final concentration in tissue culture media. The concentration of alcohol in the medium ranged from 0.1 to 0.5%. Controls were treated identically, but were incubated without resveratrol.

Upon addition of the medium to the cultures and at 24 hours time periods thereafter, i.e., 0 hours, 24 hours, 48 hours, and 72 hours after addition of the drug, cells and medium were frozen at −70° C. Samples were then thawed, sonicated and titrated on Vero cells to determine the number of plaque forming units (pfu's) of virus produced by each culture.

As shown in FIG. 1, the number of pfu's produced in the control cultures infected with an moi of 1 reaches peak production at approximately 48 hours after infection. At this time, the system is exhausted, i.e., active virus has infected and destroyed not only those cells infected during the initial one hour of incubation but also those cells which became infected with virus released by the initially-infected cells. The lack of increase observed in the control cultures at 72 hours treatment indicates that the virus production has peaked, due to the lack of viable cells in which to reproduce.

As shown in FIG. 1, treatment of cells with 50 μg/ml of rveratrol inhibited formation of infectious virus particles in HSV-1 infected cells by more than 99% at 24 hours. By 72 hours, infectious HSV particles were virtually undetectable in cultures continuously incubated in the presence of 50 μg/ml of resveratrol.

These results also demonstrate that inhibition of virus replication by resveratrol is dose dependent. Treatment with 25 μg/ml resveratrol reduced new virus production by only 95%, while treatment with 10 μg/ml of resveratrol had little to no effect on formation of infectious virus particles.

B. Cultures of human fibroblasts (MRC-5 cells) grown to confluence in Eagle's basal medium supplemented with 10% fetal bovine serum, 0.075% $NaHCO_3$, and 50 μg/ml gentamycin sulfate were infected with HSV-1 at an moi of 1 as described above in part A. The infected cultures were incubated at 37° C. for 72 hours in medium lacking resveratrol (control cultures) or containing 50 μg/ml of resveratrol. The number of plaque-forming units produced in control cultures and cultures treated with resveratrol were determined as described above. The results indicated that treatment with 50 μg/ml ml resveratrol inhibits formation of infectious virus particles by greater than 99% in the virus-infected human fibroblasts.

Example 2

Inhibiting Formation of Infectious HSV-2 Particles by Treatment with Resveratrol Cultures of Vero cells were infected with HSV-2 at an moi of 1 as described above in Example 1A and incubated for 72 hours in medium lacking resveratrol or containing 50 μg/ml of resveratrol. The number of plaque-forming units produced control cultures and cultures treated with resveratrol were determined as described above. The results indicated that such treatment inhibits replication of HSV-2 in virally-infected cells by more than 99%.

Example 3

Inhibitinoz Formation of Infectious HSV-1 Particles by Contacting Cells with Resveratrol Prior to or Durino an Earlv Stage in Replication.

Vero cell cultures were infected with HSV-1 as described above in Example 1A except that the cells were infected with virus at an moi of 10. Under these conditions nearly all of the cells are infected with virus during the initial one hour incubation period. Following removal of unattached virus, the virally-infected cultures were incubated in control medium lacking resveratrol or medium to which resveratrol at a final concentration of 50 μg/ml had been added at 1, 3, 6, or 9 hours after removal of the unattached virus. At 24 hours after infection, the number of pfu's present in the cells and medium of untreated and resveratrol-treated cultures was determined.

Figure 2:
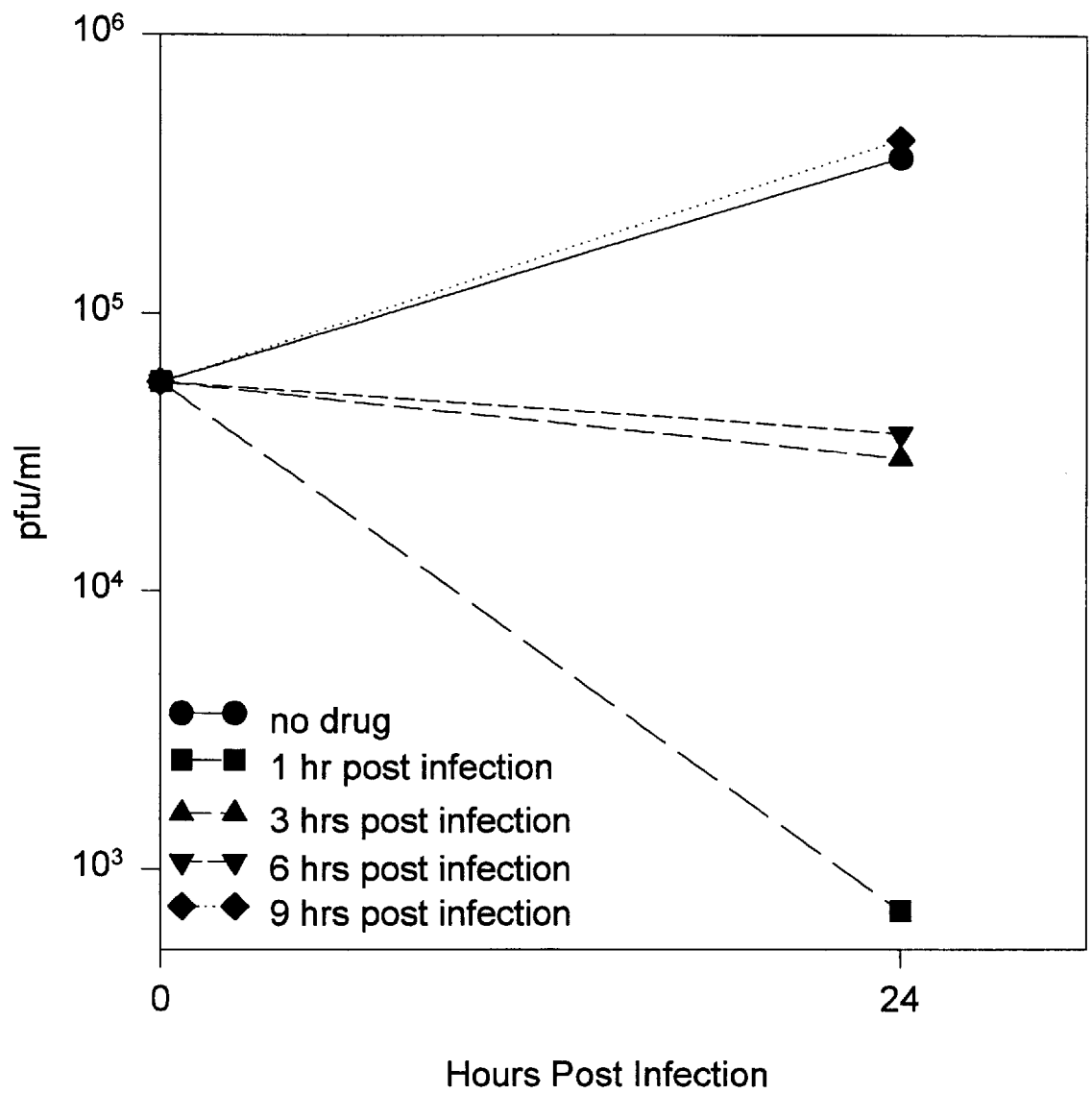
FIG. 2 is a graph showing the extent of HSV-1 replication in virus-infected cells treated with resveratrol at different times following infection.

The results presented in FIG. 2 demonstrate that resveratrol is most effective when administered to virally-infected cells during the early stages of viral replication. In cultures treated with resveratrol at one hour after infection, production of virus was reduced by more than 99%. In cultures treated with resveratrol at 3 or 6 hours after infection, the production of virus was inhibited by approximately 90%. When the hydroxylated stilbene was added 9 hours after infection, formation of infectious virus particles was not inhibited.

To determine whether resveratrol blocks formation of infectious herpes virus particles by directly inactivating the virus, a standard inoculum of HSV-1 was mixed with 10 or 50 μg/ml of resveratrol in medium, with 0.5% ethanol in medium, or with media alone and placed at room temperature. The number of residual pfti's present at 1, 10, 30, and 60 minutes after addition of each respective solution to the virus was determined by plaque assay. The results demonstrated that resveratrol did not directly inactivate HSV.

Example 4

Inhibiting Formation of Infectious HSV-2 Particles by Contacting Cells with Resveratrol Prior to or During an Early Stage in Replication.

Vero cells were infected with HSV-2 at an moi of 10 and the effect of treatment with resveratrol at 1, 3, 6, or 9 hours after removal of the unattached virus was determined as described in Example 3. The results were the same. Administration of resveratrol to the cells within the first 6 hours after infection blocked replication of HSV-2, while treatment with the hydroxylated stilbene at 9 hours after infection had little to no effect on formation of infectious HSV-2 particles.

Example 5.

Inhibiting HSV Replication

Vero cells were grown to confluence and infected with HSV-1 at an moi of 1 and then incubated in media lacking resveratrol (control cultures) or in media containing resveratrol at a concentration of 50 μg/ml. One set of infected cells was maintained in resveratrol for a period of 72 hours. In another set of infected cells the resveratrol-containing media was replaced with media lacking resveratrol at 24 hours. In another set of cells the resveratrol-containing media was replaced with media lacking resveratrol at 48 hours after infection. The number of infectious HSV particles produced by each set of infected cells was determined by plaque assay.

Figure 3:
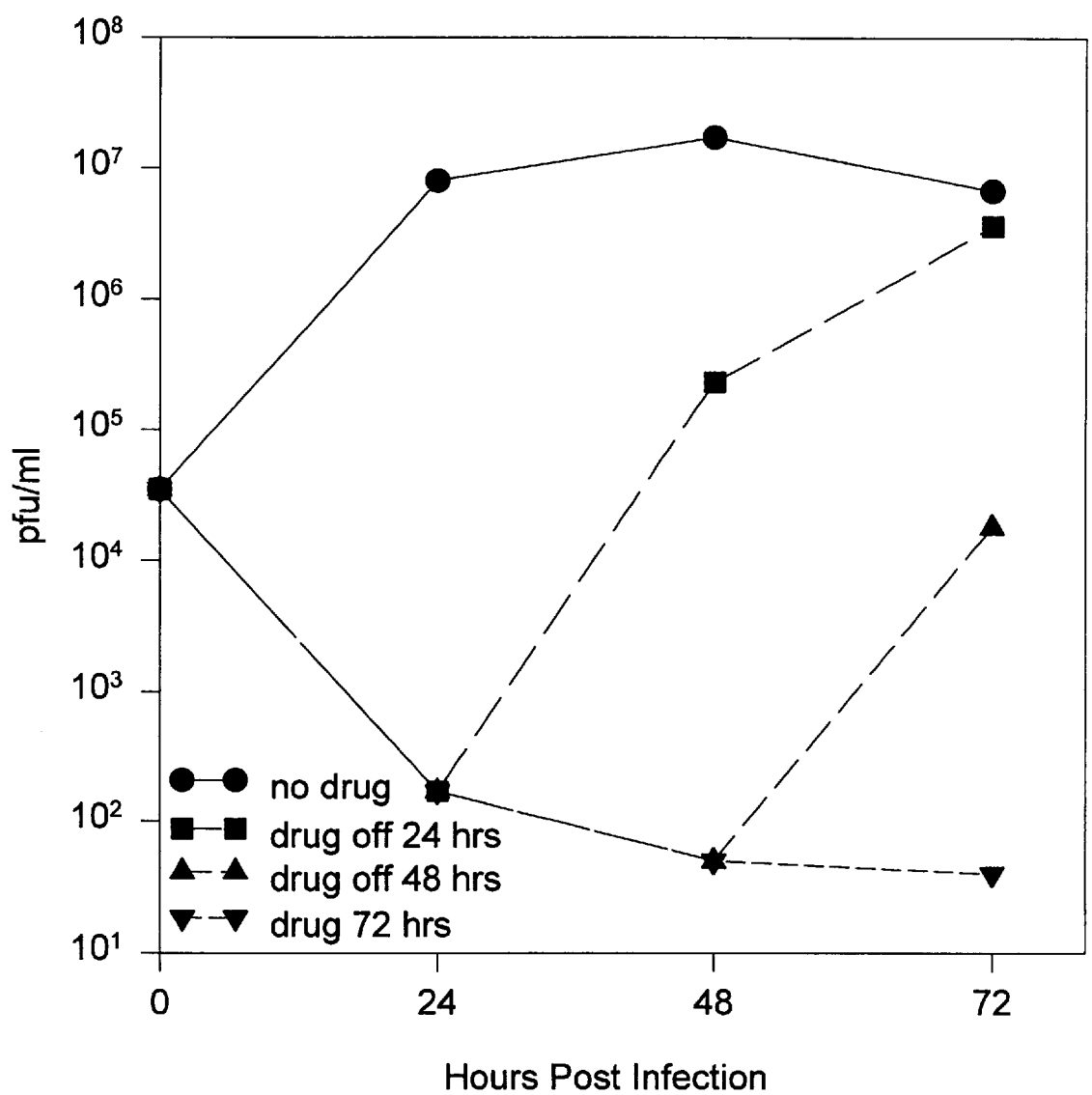
FIG. 3 is a graph depicting the reversibility of the inhibitory cffcct of resveratrol on HSV-1 replication in virus-infected cells.

The results shown in FIG. 3 demonstrate that the inhibitory effect of resveratrol on HSV replication in virus infected cells is reversible. Accordingly, continuous treatment of HSV-infected cells with resveratrol maintains the virus in a non-infectious state. Discontinuing the resveratrol treatment allows replication of the virus to proceed in what appears to be a normal fashion. The same results were obtained with HSV-2 (data not shown). The results presented in FIG. 3 also suggest that HSV replication in the resveratrol treated cells was blocked at an early phase, i.e., replication of HSV had not progressed past the stage where cells are so damaged that they are unable to support replication of this herpes virus.

The results presented in FIG. 3 also indicate that exposure of mammalian cells to 50 μg/ml resveratrol for a prolonged period of time does not kill the cells. Cell viability studies confirmed that treatment of uninfected Vero cells with 50 μg/ml resveratrol for 24 hours was not toxic. When uninfected Vero cells were incubated in medium containing 100 μg/ml resveratrol for 24 hours, an 18% reduction in Vero cell viability was observed.

Example 6

Characterizing Viral Proteins Produced in the Presence of Resveratrol

ICP-4 is an immediate-early regulatory protein of HSV-1 that is required for efficient replication of this virus. To determine whether ICP-4 production is altered by treatment with resveratrol, Vero cells were infected with HSV-1 at an moi of 1 and incubated in control medium or medium containing 50 μg/ml resveratrol for 24 hours. Infected cells were scraped from the flask, collected by centrifugation, and resuspended in cold tris-buffered saline, pelleted by centrifugation, and the cell pellet frozen at −70° C. Proteins were extracted from the thawed pellets, separated by 6–15% SDS-PAGE, and assayed on a Western blot by reacting with mouse monoclonal antibody to ICP-4 from Goodwin Institute for Cancer Research Inc., Fl.

Figure 4:
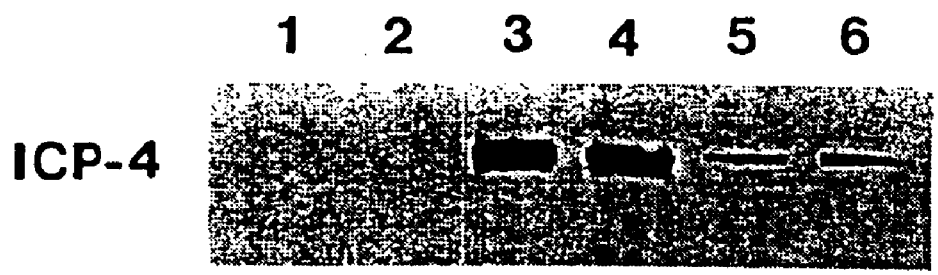
FIG. 4 is a graph depicting the effect of treatment with resveratrol on the accumulation of ICP-4 in HSV-1 infected cells.

As shown in FIG. 4, treatment of HSV-infected cells with resveratrol significantly reduced synthesis of ICP-4, a major regulatory protein. These results confirm that treatment with resveratrol inhibits synthesis herpes viruses at an early phase in the replicative scheme. These results also indicate that cultured cells treated with reseveratrol are a useful model system for characterizing the herpes virus gene products that are made during the immediate early phase and early phase of HSV replication.

Example 7

Maintaining HSV in a Latent Stage in Organ Culture.

SJH1 (Charles Rivers Laboratory) mice were anesthetized with metofane and both corneas lightly scratched with a 30 gauge needle. A 50 μg inoculum of $10^4$ pfu of HSV-1 was placed on the eye surface which was then closed and gently massaged. The animals were rested for not less than 30 days. The animals were euthanized with $CO_2$, and the left and right trigeminal ganglia harvested. The ganglia were aseptically removed and placed in separate wells of a 12 well tissue culture plate containing tissue culture media with 50 μg/ml of resveratrol or without resveratrol. On each day of the following 10 days, the fluid from each well was collected, frozen, and replaced with fresh media. At the end of ten days, each sample of collected medium was tested for the presence or absence of infectious virus usinig a plaque assay.

The results are shown in Table 1 below.

TABLE 1

The Effect of Resveratrol on Reactivation of HSV from Latently-infected Trigeminal Ganglia
Number Reactivated[1]

| Left Ganglia - No Resveratrol | Right Ganglia - With Resveratrol |
|---|---|
| 8 | 0 |

[1]Left and right trigeminal ganglia were removed from each mouse and incubated for ten days in media with or without resveratrol. Samples were taken and tested daily for infectious virus. A positive result is the appearance of infectious virus in any of the ten day test samples.

As shown in Table 1, ganglia from 8 of the animals released infectious virus when incubated in medium lacking resveratrol, while no virus was released from the corresponding ganglia that had been incubated in medium containing resveratrol. These results indicate that organ cultures incubated in medium containing resveratrol are good model systems for studying latency of herpesvirus.

Example 8

Treating HSV Infections with a Topical Composition Comprising Resveratrol.

Female SKHI hairless mice were obtained from Charles River Laboratory. The animals were anesthetized with metofane and lightly scratched once on their back with a 30 gauge needle. A cotton swab saturated with HSV-1, at a concentration of $10^7$ pfu/ml in media, was applied to the scratch for a few seconds. The animals were returned to their cage and, after one hour, were treated with resveratrol by soaking a cotton swab in resveratrol at a concentration of 50 μg/ml in Media 199 and applying it to the scratch site for several seconds. The virus-infected site was treated with the resveratrol containing solution as described above three times a day. The animals were monitored daily for lesion formation according to the following schedule: 0 =no lesion; 1+=erythema; 2+=erythema, limited vesicle formation 3+=erythema, moderate vesicle formation, few ulcers; and 4+=erythema, extensive vesicle formation, multiple ulcers, scab formation. The results are shown in Table 2 below.

TABLE 2

Effect of Resveratrol on HSV-1 Lesion Formation in the Skin of Hairless Mice

| | Day 5 | | Day 8 | | Day 9 | | Day 10 | | Day 11 | | Day 12 | | Day 15 | |
|---|---|---|---|---|---|---|---|---|---|---|---|---|---|---|
| | L[3] | R | L | R | L | R | L | R | L | R | L | R | L | R |
| Resveratrol-Treated[1] | .7+[4] | 0 | 3+ | 0 | 2.3+ | .33+ | 2.7+ | 1.3+ | 2.3+ | 1+ | 1.7+ | 1+ | .33+ | 0 |
| Control[2] | 1+ | 0 | 3+ | 2+ | 4+ | 3+ | 4+ | 3+ | 4+ | 3+ | 2+ | 1+ | 0 | 0 |

[1]Average of three animals.
[2]One animal.
[3]L = left side; R = right side.
[4]0 = no lesions; 1+ = erythema; 2+ = erythema, limited vesicle formation; 3+ = erythema, moderate vesicle formation, few ulcers; 4+ = erythema, extensive vesicle formation, multiple ulcers, scab formation.

As shown in Table 2, HSV1-infected control animals and HSV-1 infected animals treated with resveratrol as described above began showing signs of infection five days after being exposed to the virus. Treatment with resveratrol was stopped at that time for two days to allow lesions to fully develop. Lesions first began to appear on the left side of the animal and then spread to the right side. In both resveratrol-treated and control animals, lesions developed on both sides, but lesion development in resveratrol-treated animals appeared to lag behind the control in both time of appearance and extent of tissue damage. Both groups of animals appeared to recover at about 15 days after exposure to the virus. These results demonstrate that treatment with resveratrol reduces the severity of HSV-1 infections.

What is claimed is:

1. A method of inhibiting formation of infectious herpes virus particles in a host cell infected with a herpes virus comprising administering resveratrol to the herpes virus-infected host cell.

2. The method of claim 1 wherein resveratrol is administered in an amount effective to block replication of the herpes virus in the infected cell.

3. The method of claim 1 wherein resveratrol is administered within 6 hours of infection of the host cell with the herpes virus.

4. The method of claim 1 wherein the herpes virus is selected from the group consisting of HSV-1, HSV-2, CMV and VZV.

5. The method of claim 1 wherein the herpes virus is selected from the group consisting of HSV-1 and HSV-2.

6. A method of treating a subject having a helpes infection induced by a herpes virus selected from the group consisting of HSV-1, HSV-2, CMV and VZV, said method comprising administering a pharmaceutical composition comprising a therapeutically effective amount of a tri-hydroxylated stilbene to a site of infection on said subject.

7. A method of treating an infection induced by a herpes virus selected from the group consisting of HSV-1, HSV-2, CMV and VZV, said method comprising administering a pharmaceutical composition comprising a therapeutically effective amount of resveratrol or a derivative thereof to a site of infection on a subject.

8. The method of claim 7 wherein the pharmaceutical composition further comprises a topical carrier and administration is by topical administration to or proximate to a site of infection on the skin of said subject.

9. The method of claim 7 wherein the site of infection is in an eye of the subject and administration is to the eye of said subject.

10. The method of claim 7 wherein the site of infection is in the oral cavity or on a lip of the subject and administration is to or proximate to the site of infection in the oral cavity or lips of said subject.

11. The method of claim 7 wherein the site of infection is in the vagina or anus of the subject and administration is by vaginal insertion or anal insertion.

12. The method of claim 8 wherein the herpes virus infection is caused by HSV-1 or HSV-2.

13. The method of claim 7 wherein the pharmaceutical composition is administered to an infected site during the prodromal stage of infection.

14. The method of claim 7 wherein the pharmaceutical composition is applied at or proximate a known site of infection or a site which is suspected of being infected.

15. A method of reducing the cytopathic effect of HSV-1 or HSV-2 on a host cell which comprises administering resveratrol to the host cell in an amount sufficient to inhibit replication of HSV-1 or HSV-2 within the host cell.

16. A method of treating a patient infected with a herpes virus comprising:

administering a pharmaceutical composition comprising a therapeutically effective amount of resveratrol or a derivative thereof to a current herpes virus-infected site or to a site of a prior herpes virus-induced lesion on a patient infected with a herpes virus.

* * * * *

UNITED STATES PATENT AND TRADEMARK OFFICE
CERTIFICATE OF CORRECTION

PATENT NO. : 6,197,834 B1
DATED : March 6, 2001
INVENTOR(S) : John Docherty

It is certified that error appears in the above-identified patent and that said Letters Patent is hereby corrected as shown below:

Column 11,
Line 28, after "having a" delete "helpes" and insert --- herpes ---.

Signed and Sealed this

Seventh Day of August, 2001

*Attest:*

*Nicholas P. Godici*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,197,834 B1
DATED : March 6, 2001
INVENTOR(S) : John Docherty

It is certified that error appears in the above-identified patent and that said Letters Patent is hereby corrected as shown below:

Column 4,
Line 22, after "joined by a", delete "methylene" and insert -- ethylene --.

Signed and Sealed this

Fourth Day of December, 2001

Attest:

*Nicholas P. Godici*

NICHOLAS P. GODICI
*Attesting Officer*   *Acting Director of the United States Patent and Trademark Office*